United States Patent [19]

Swisher

[11] Patent Number: 5,601,541
[45] Date of Patent: Feb. 11, 1997

[54] FOOTSTAND FOR CHEST DRAINAGE UNIT

[75] Inventor: David R. Swisher, St. Louis, Mo.

[73] Assignee: Sherwood Medical Company, St. Louis, Mo.

[21] Appl. No.: 359,486

[22] Filed: Dec. 20, 1994

[51] Int. Cl.$^6$ .................................................. A61M 1/00
[52] U.S. Cl. .................................. 604/322; 128/DIG. 24; 248/685; 248/188.7
[58] Field of Search ........................... 604/317, 322–26, 604/319; 128/760, DIG. 24; 248/685, 688, 188.7, 188.6, 167, 436

[56] References Cited

U.S. PATENT DOCUMENTS

| | | | |
|---|---|---|---|
| 892,413 | 7/1908 | Freeman | 248/167 |
| 2,176,235 | 10/1939 | Woodard | 604/322 |
| 2,647,381 | 8/1953 | Lamounette | 248/167 |
| 3,199,825 | 8/1965 | Bellows | 248/397 |
| 4,449,969 | 5/1984 | Schweizer | 604/322 |
| 4,955,873 | 9/1990 | Rajlevsky | 604/322 |
| 5,161,768 | 11/1992 | Sarabin | 248/188.7 |
| 5,267,712 | 12/1993 | Shen | 248/188.7 |

Primary Examiner—David Isabella
Assistant Examiner—Mark O. Polutta
Attorney, Agent, or Firm—David A. Warmbold; Montgomery W. Smith

[57] ABSTRACT

A footstand for stabilizing or securing a body of a medical device against overturn. The body may especially be a chest drainage unit designed and configured to receive and collect fluids from a medical patient. The invention comprises a two leg component rotatable footstand which incorporates a gear driving mechanism which operates between the legs to simplify the action of pulling out the respective legs of the footstand. The gear driving mechanism allows the medical technician to activate the footstand by simply pulling out either the front or back leg to its stabilizing position, the other leg will automatically be rotated into its stabilizing position. A detent is provided which will provide a secure "click" sound so that a medical technician will know the legs have been pulled out away from the CDU a sufficient distance to provide the proper stabilization for the CDU. The preferred embodiment of the CDU footstand shows the leg components positioned on the bottom of the CDU body, however an alternate embodiment shows the disclosed footstand being positioned on either the right or left side of the CDU body.

16 Claims, 3 Drawing Sheets

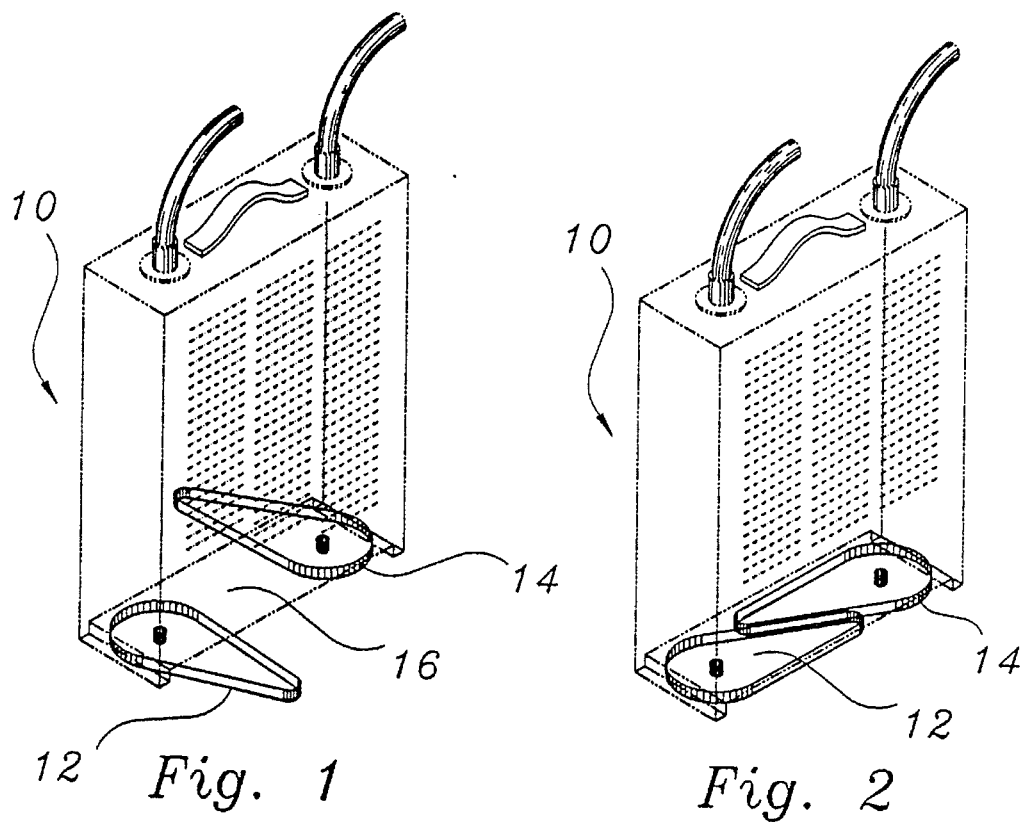
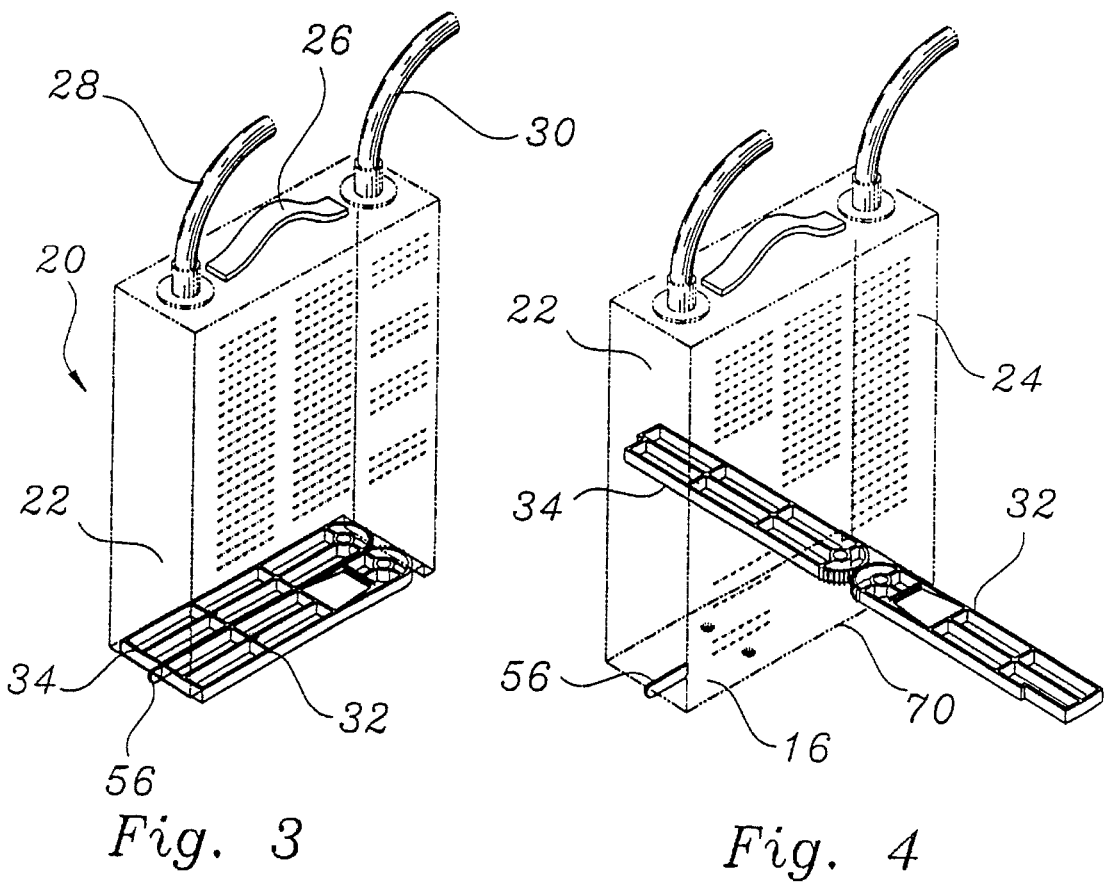

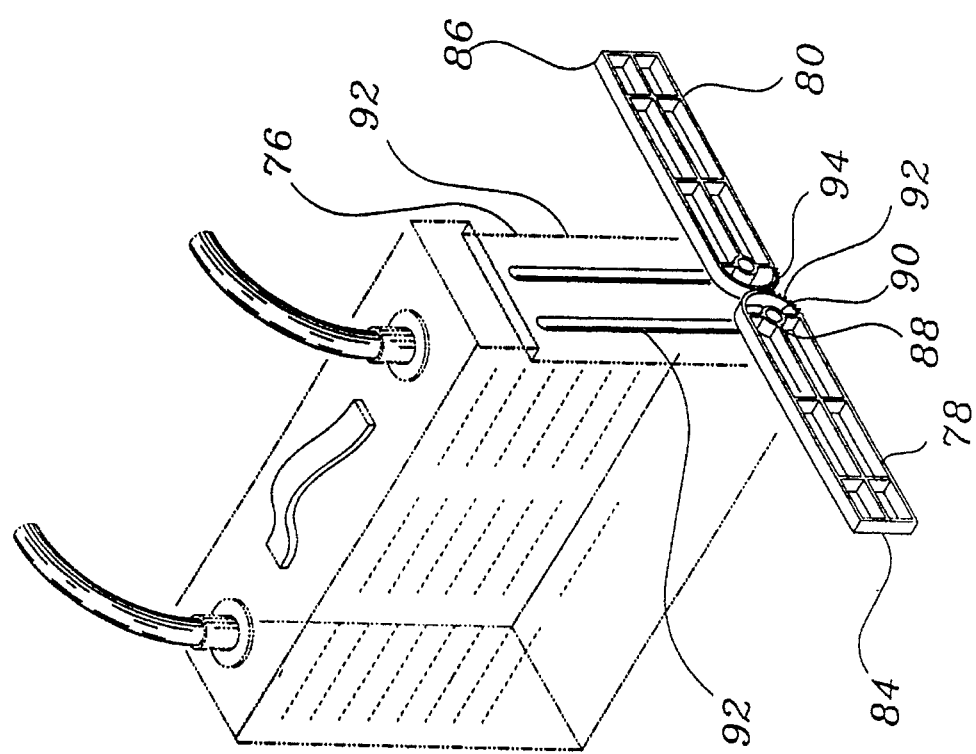
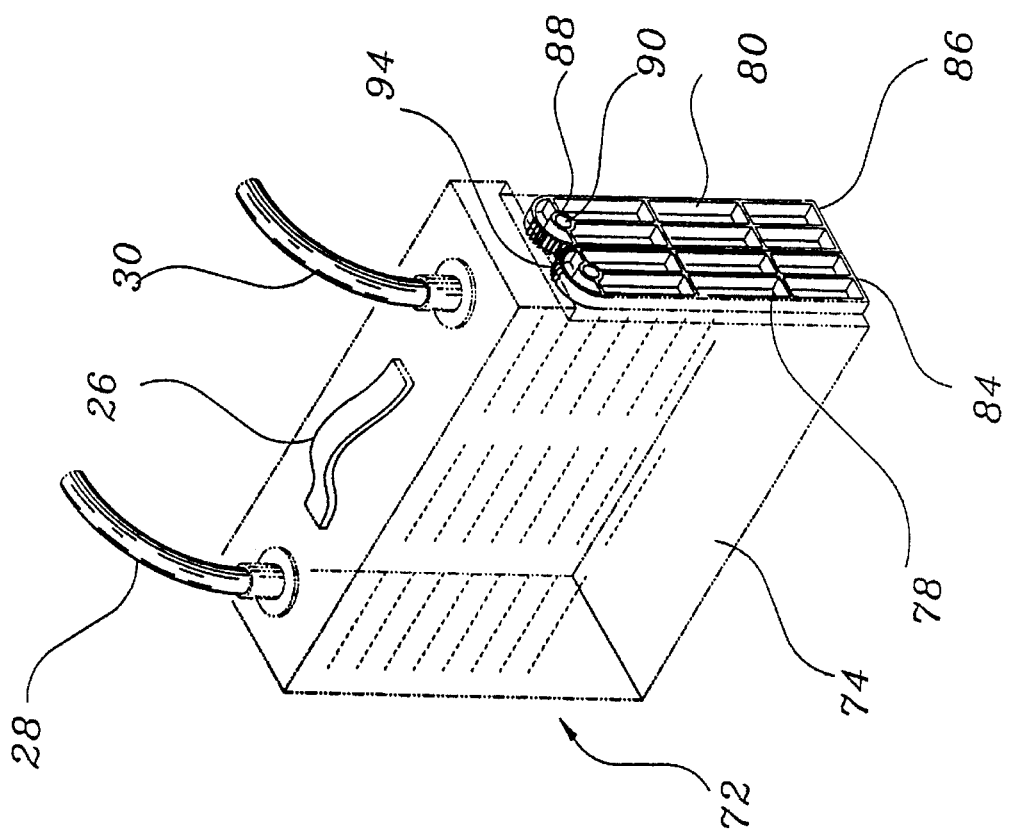

5,601,541

FOOTSTAND FOR CHEST DRAINAGE UNIT

BACKGROUND OF THE INVENTION

1. Field of the Invention

The present invention relates generally to a footstand or support stand for free standing medical devices and, more particularly, the invention relates to a footstand suitable in use with a drainage unit to prevent such unit from being upset or overturned. The footstand finds a preferred use in stabilizing a chest drainage unit (CDU), used chiefly during surgical procedures and for post operative patient care, for receiving and collecting fluids drained from the patient, by securing the CDU in an upright position.

2. Prior Art

There have been a number of devices introduced in the market place for use as a base or stand in an effort to keep a CDU or other drainage device in an upright position. U.S. Pat. No. 4,955,873 to Rajlevsky discloses one such unit. However, Rajlevsky only discloses the use of a single rotating base member which is capable of extending only a short distance on either side of the drainage device to provide the required support for such drainage device. A second drainage receptacle with footstand is shown in U.S. Pat. No. 4,449,969 to Schweizer. The rotating footstand shown in Schweizer is very similar to that shown in Rajlevsky including the same disadvantages discussed above.

A further prior art CDU with footstand is illustrated in FIGS. 1 and 2 wherein the CDU 10 has two base supporting members or legs 12 and 14, one at either end of the base of the CDU. Each leg 12 and 14 is provided with a length generally equal to the width of the CDU base. Therefore, unlike the prior art footstands discussed above, each leg of the prior art device shown in FIG. 1 is as long as the CDU base is wide thereby providing leg supporting surfaces extending a greater distance on either side of the supported CDU such that the CDU has an improved stability. However, to extend the two base supporting members 12 and 14, it is necessary to rotate each supporting member separately into its base stabilizing position. And, when transporting the CDU, it will be necessary to rotate each supporting member back again into its non-stabilizing positions.

SUMMARY OF THE INVENTION

It is an object of the present invention to provide a footstand or support stand for a free standing medical device which guards against device overturn and where the footstand can be activated into and out of its stabilizing position in a quick and easy fashion.

It is another object of the present invention to provide a footstand for a chest drainage unit (CDU) which can be rotated into and out of its CDU stabilizing position in a quick and easy manner by an intended user in a one handed single motion process.

It is another object of the present invention to provide a fold away footstand for a CDU which when in its non-stabilizing position does not protrude outward of the body of the CDU and when in its stabilizing position provides two legs, one leg extending in front of and one leg extending in back of the CDU to provide a CDU in a stable upright position.

It is yet another object of the present invention to provide a footstand for a CDU which provides the maximum area of supporting surface in a pair of supporting members which can be activated in a single motion into both extended and retracted positions by an intended user of the CDU.

These and other objects are realized in a footstand for stabilizing or securing a body of a medical device against overturn. The body may especially be a chest drainage unit designed and configured to receive and collect fluids from a medical patient. The invention comprises a two leg component rotatable footstand which incorporates a gear driving mechanism which operates between the legs to simplify the action of pulling out the respective legs of the footstand. The gear driving mechanism allows the medical technician to activate the footstand by simply pulling out either the front or back leg to its stabilizing position, the other leg will automatically be rotated into its stabilizing position. A detent is provided which will provide a secure "click" sound so that a medical technician will know the legs have been pulled out away from the CDU a sufficient distance to provide the proper stabilization for the CDU.

To reposition the two legs of the footstand, the medical technician releases the detent by finger pressure or simply pushing either the front or back leg towards the CDU body with sufficient force to overcome the detent. Upon inward motion of one of the legs towards the CDU body, the other leg will also move inwards toward the CDU body because of the gear drive mechanism until the two legs are snapped back into their original retracted position underneath the CDU body such that no portion of either leg extends outside the side boundaries of the CDU body.

The preferred embodiment of the CDU footstand shows the leg components positioned on the bottom of the CDU body, however an alternate embodiment shows the disclosed footstand being positioned on either the right or left side of the CDU body. In this embodiment, the two legs would have a similar gear driver mechanism to allow both legs to be actuated into their stabilizing position and deactivated into their closed or non-stabilizing position by movement of a single leg component by the medical technician. Additionally, the pivot of each leg would be allowed to slide in respective parallel vertical slots to allow the leg components of the footstand to move into their stabilizing positions. A detent is also provided in both the footstand's fully open and closed positions to assist in holding the leg components in their respective stabilizing and non-stabilizing positions.

The various features of novelty which characterize the invention are pointed out with particularity in the claims annexed to and forming a part of this disclosure. For a better understanding of the invention, its operating advantages and specific results obtained by its use, reference should be made to the corresponding drawings and descriptive matter in which there is illustrated and described various embodiments of the invention.

BRIEF DESCRIPTION OF THE DRAWINGS

FIGS. 1 and 2 are perspective views of a footstand for a CDU of the prior art showing the leg components in stabilizing and non-stabilizing positions.

FIG. 3 is a perspective view of a footstand for a CDU (shown in phantom) in accordance with the principles of the present invention, showing the footstand in a first inoperative non-stabilizing position.

FIG. 4 is a view of the footstand and CDU substantially as shown in FIG. 3 but with the footstand shown rotated into a second operative position stabilizing the CDU in an upright position.

FIG. 7 is a perspective view of an alternate embodiment of the footstand for a CDU, in accordance with the principles of the present invention, showing the footstand in a first inoperative non-stabilizing position.

FIG. 8 is a perspective view of the footstand and CDU of FIG. 7, but with the footstand shown positioned in a second operative position stabilizing the CDU in an upright position.

DETAILED DESCRIPTION OF THE INVENTION

Figure 6:
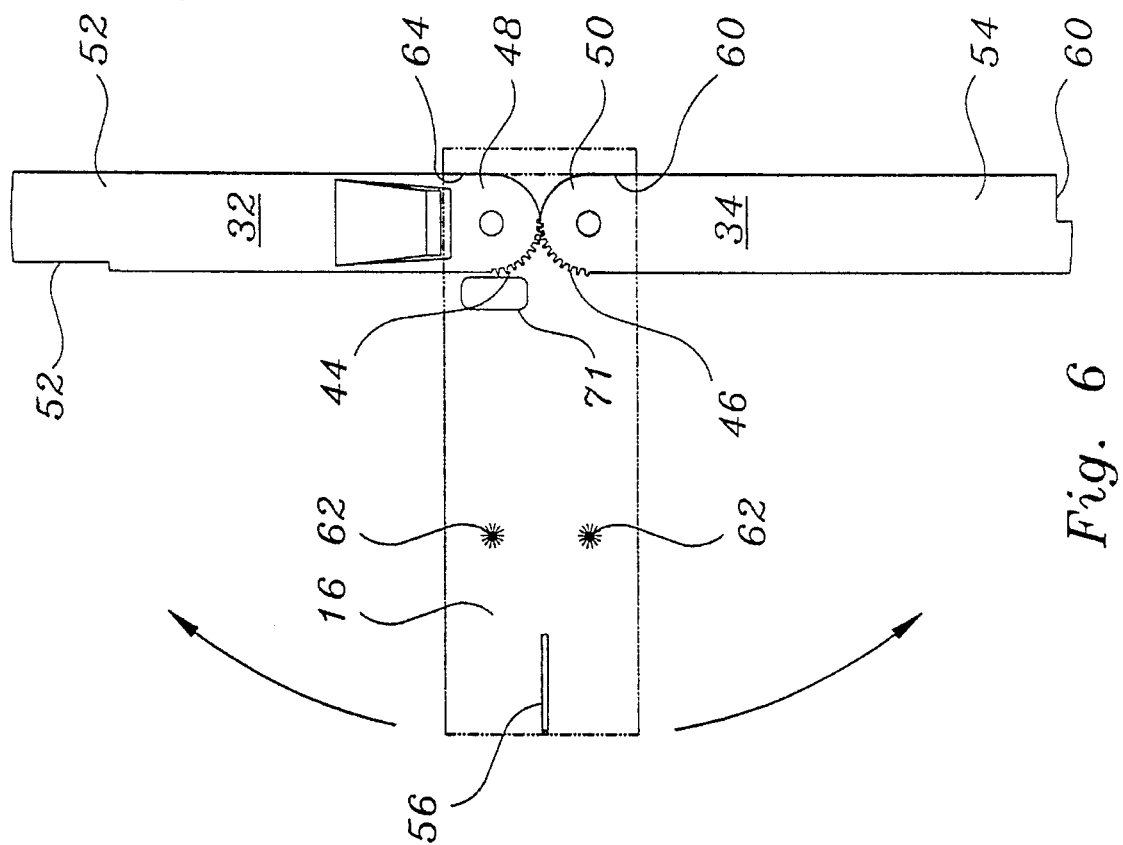
FIG. 6 is an enlarged plan view of the bottom of the footstand and CDU substantially as shown in FIG. 4, showing the footstand in its second operative position for stabilizing the CDU.

The description presented herein refers to the accompanying drawings in which like reference numerals refer to like parts throughout the several views. First, turning to FIGS. 1 and 2, a chest drainage unit (CDU) of the prior art is shown and is referred to generally at 10. The CDU has two base supporting members or legs 12 and 14, one at either end of the base 16 of the CDU. Each leg 12 and 14 is provided with a length generally equal to the width from side to side of the CDU base 16. To extend the two base supporting members 12 and 14, it is necessary to rotate each supporting member or leg separately into its base stabilizing position. To reposition the legs for transportation of the CDU it will be necessary to rotate each leg back again into their non-stabilizing positions.

Now referring to FIGS. 3 and 4, there is illustrated a perspective representation of a chest drainage unit (CDU) 20 of the preferred embodiment, with housing portion 22 forming a collection chamber 24 for collecting fluids drained from a patient, handle 26, patient connection tube 28 and suction source connection tube 30, all shown in phantom, having base portion 16 and two base supporting members or legs 32 and 34. In FIG. 3, legs 32 and 34 are shown in a first inoperative non-stabilizing or stored position such that the legs are not yet deployed into their CDU body stabilizing positions. In FIG. 4, there is shown a view similar to that shown in FIG. 3, however, the base supporting members or legs 32 and 34 are now shown in a fully deployed, second operative body stabilizing position.

Figure 5:
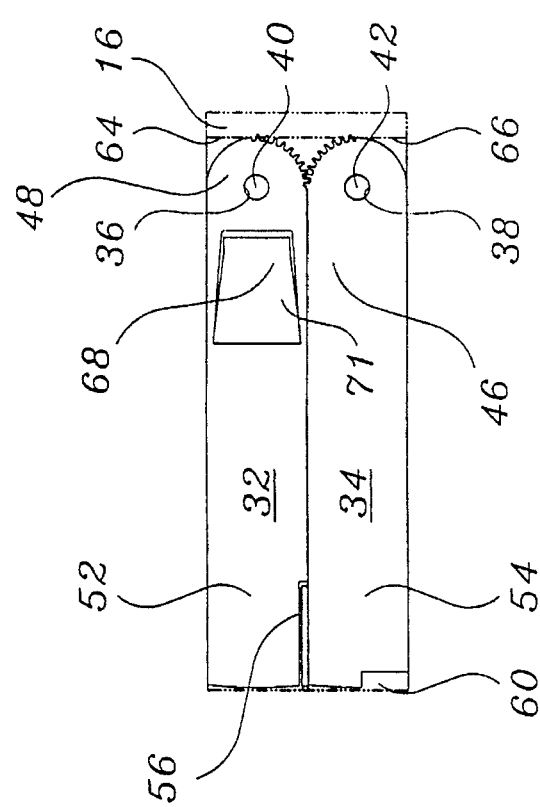
FIG. 5 is an enlarged plan view of the bottom of the footstand and CDU substantially as shown in FIG. 3, showing the footstand in its first inoperative non-stabilizing position.

Referring now to FIGS. 5 and 6 wherein enlarged views of the base supporting members or legs 32 and 34 are shown in fully deployed and secured positions. In FIG. 5, the legs 32 and 34 can be seen in greater detail. Each leg 32 and 34, are shown having pivot holes 36 and 38, respectively, which receive pivot pins 40 and 42, respectively, depending from the base 16 of the CDU. The pins 40 and 42 are rotationally secured within pivot holes 36 and 38 in a normal fashion as is known in the art. A plurality of gears 44 and 46 are provided on a proximal end 48 and 50 of each leg 32 and 34, respectively. Each leg 32 and 34 also has a distal end 52 and 54, respectively, which distal ends are shown in FIGS. 3 and 5 to be received underneath the base 16 of CDU 20. The gears 44 and 46 of legs 32 and 34 interact with each other such that upon movement of either the distal end 52 of leg 32 or the distal end 54 of leg 34 in a radial direction respective to their pivot holes away from the base 16 of CDU, the gear of one leg will move the other leg in a similar radial movement away from the base 16 of CDU. Arrows are illustrated on FIG. 6 showing the direction of travel of legs 32 and 34 to move said legs into their second stabilizing position. In this fashion, a medical technician can move both legs 32 and 34 from their first non-stabilizing position to their second base stabilizing position by simply grasping and rotating only one of the legs.

In FIG. 6, the legs 32 and 34 are shown in their fully deployed, base stabilizing position. A base support 56, depending downwardly from the base 16 of CDU 20 is provided to support one side of the CDU when the legs 32 and 34 are fully deployed. A cutout 58 is provided on the side of leg 32 near its distal end 52 so that when legs 32 and 34 are in their first inoperative position, leg 32 can be fit adjacent base support 56 such that leg 32 will still fit completely underneath the base 16 of CDU 20. Furthermore, leg 34 is provided with a cutout 60 on its distal end 54 to assist in manual grasping by a medical technician of the distal end of leg 34 so that the legs 32 and 34 can be moved from the first inoperative non-stabilizing position to the second operative, base stabilizing position.

In FIG. 6, a pair of bumps or detents 62 are shown which depend slightly downward from the base 16 of CDU 20 to assist in holding legs 32 and 34 in their first inoperative positions underneath the base 16 of CDU 20 as shown in FIG. 5.

Referring again to FIG. 6, there is shown the legs 32 and 34 in their fully deployed, second operative body stabilizing position. Legs 32 and 34 have been manually rotated from their first to second position in the direction shown by the arrows. Rotation of legs 32 and 34 beyond the fully deployed position shown is prevented because legs 32 and 34 contact wall surfaces 64 and 66, respectively of base 16. Leg 32 includes a resilient detent 68 or like projection disposed therein, which detent acts to retain leg 32 in its fully deployed position as shown in FIG. 6. During rotation of leg 32 from its first to second position, detent 68, having a sloping or ramp face, coacts with a lower surface wall 70 of base 16 and is deflected downward. Upon full rotation of leg 32 to its base stabilizing position, detent 68 returns to its predeflected state, rising slightly above the lower segment of wall 70 and essentially coming into abutting relationship with wall 70, thereby retaining leg 32 in its fully deployed position. Detent 68 can be released from its blocking position against wall 70 by depressing detent 68 to release any interference between wall 70 and detent 68 such that detent 68 will clear the lowermost portion of wall 70 allowing for manual rotation of leg 32 or by simply manually exerting a little more force on the distal end 52 of leg 32 in a direction towards the base support 56 to return the legs 32 and 34 to their first non-stabilizing position as shown in FIGS. 3 and 5. Referring to FIG. 6, a small depression 71 is seen on base 16 such that when leg 32 is returned to the first non-stabilizing position as shown in FIG. 5, the detent 68 will slide into the depression 71 which also assists in holding legs 32 and 34 secure in the first non-stabilizing position.

In FIG. 6, the legs 32 and 34 are shown in their open or deployed position generally 90° from their closed or inoperative position shown in FIG. 5. However, it may be desirable to open the legs 32 and 34 farther than 90° and, therefore, wall surfaces 64 and 66 could be configured to allow legs 32 and 34 to open to greater than 90°. Likewise, detent 68 could be configured so that it would snap into its blocking position at a point where legs 32 and 34 are in a greater than 90° position, if desired.

In an alternate embodiment, shown in FIGS. 7 and 8, a CDU 72 is shown having a collection chamber 74 for collecting fluids drained from a patient, handle 26, patient connection tube 28 and suction source connection tube 30, all shown in phantom, having a side wall 76 and two base supporting members or legs 78 and 80. In FIG. 7, legs 78 and 80 are shown in a first inoperative position such that legs 78 and 80 are not deployed into their CDU body stabilizing positions. The legs 78 and 80 remain within the overall boundaries of the collection chamber 74 such that no portion of said legs extend outside the boundaries or dimensions of said CDU 72. A pair of detents or bumps 82 assist in securing said legs 78 and 80 in their first inoperative position. Each leg 78 and 80 is provided with a pivot hole 88 and a pivot pin 90 which is secured within each leg member. Each pin 90 of legs 78 and 80 extend into and are slidingly affixed within a pair of slots 92 provided within side wall 76 of CDU 72 (FIG. 8).

Referring now to FIG. 8, the legs 78 and 80 are shown in a fully deployed, second operative body stabilizing position. To accomplish this movement from a first inoperative position to a second operative body stabilizing position, a distal end 84 or 86 of legs 78 or 80, respectively is manually grasped and pulled away from the collection chamber 74. Each leg 78 and 80 is provided with a plurality of cooperating gears 92 and 94, respectively so that upon movement of one leg the other leg will move in a similar fashion. The embodiment of FIGS. 7 and 8 is different from that shown in FIGS. 3–6 in that upon manual rotation of the legs 78 and 80 away from the collection chamber 74 the pivot pins 90 of said legs will travel downwardly in the slots 92 provided in side wall 76 until the legs 78 and 80 rest firmly on the ground or other flat surface where the CDU is resting. The legs 78 and 80 are prevented from over-rotation by the gear teeth 92 and 94 of legs 78 and 80, respectively which extend only partially around the proximal end of each leg. A detent (not shown) similar to the detent 68 shown in FIGS. 3–6 could be also utilized to assist in retaining the legs 78 and 80 in their first non-stabilizing and second operative base stabilizing positions.

While in accordance with provisions of the statutes there is described herein several embodiments of the invention, those skilled in the art will appreciate that changes may be made in the form of the invention covered by the claims appended hereto without departing from the scope and spirit thereof, and that certain features of the invention may sometimes be used to an advantage without corresponding use of the other features.

I claim:

1. A footstand in combination with a medical container, the medical container having a generally rectangular container, the footstand comprising:

a pair of legs pivotally secured to the container, the legs having a length generally equal to the width of the container and each leg having a proximal and distal end, the legs being allowed to rotate between a first inoperative position wherein said legs do not stabilize the container to a second operative position wherein said legs stabilize the container; and each leg having gear teeth provided thereon which interact with the gear teeth of the other leg such that when one leg is pivoted from the first non-stabilizing position to the second position stabilizing the container, the other leg is moved in a similar manner from the first position to the second position stabilizing the container.

2. The combination according to claim 1, wherein the container is a chest drainage unit (CDU) for receiving and collecting fluids from a patient.

3. The combination according to claim 2, wherein the legs are pivotally secured to the bottom of the container such that when said legs are in their first inoperative position said legs are contained underneath the CDU and when said legs are in their second operative position stabilizing said CDU, the distal end of each leg is positioned away from the container.

4. The combination according to claim 1, further comprising a detent being provided on a leg such that when said legs are positioned in the second operative position stabilizing the container, the detent contacts a portion of the container to hold said legs in the second operative position stabilizing the container.

5. The combination according to claim 3, further comprising a detent being provided on a leg such that when said legs are positioned in the second operative position stabilizing the CDU, the detent contacts a portion of the CDU to hold said legs in the second operative position stabilizing the CDU.

6. The combination according to claim 5, wherein the bottom of the CDU container is provided with a slight depression which receives said detent of said leg when said leg is in the first inoperative non-stabilizing position to prevent inadvertent movement of said legs from the first position to the second operative position.

7. The combination according to claim 6, further comprising a base support member depending from the bottom of the container of the CDU adjacent the distal end of the legs when said legs are in the first non-stabilizing position, said base support member assisting the legs in stabilizing the CDU when said legs are in the second operative position stabilizing the CDU.

8. The combination according to claim 7, wherein a leg further includes a cutout adjacent its distal end such that when the legs are in the first non-stabilizing position, said leg abuts cooperatively against said base support member to allow said legs to fit completely underneath said CDU.

9. The combination according to claim 2, wherein the legs are pivotally attached to the side of the container, the pivots being allowed to slide in a pair of parallel slots provided in the side of the container such that when said legs are in the first inoperative non-stabilizing position said legs are parallel and adjacent each other, and when the distal end of either leg is pulled out and radially away from the container, the other leg moves in a similar manner due to the interaction between the respective gear teeth of said legs while the pivots of each leg slides downwardly in their respective slots until the legs have rotated through a complete 90 degrees and the legs are in the second operative position stabilizing the CDU.

10. A chest drainage unit (CDU) defining a chamber for receiving and collecting fluids from a patient, the CDU comprising:

a container having four sides, a top and a bottom, and having a fluid inlet and a fluid outlet;

a pair of legs pivotally secured to the container, the legs having a length generally equal to the width of the container and each leg having a proximal and distal end, the legs being allowed to rotate about their proximal end between a first inoperative position wherein said legs do not stabilize the container to a second operative position wherein said legs stabilize the container; and each leg having gear teeth provided about a portion of their proximal end which interact with the gear teeth of the other leg such that when one leg is pivoted from the first inoperative position to the second operative position stabilizing the container, the other leg will also pivot from the first inoperative position to the second operative position stabilizing the container.

11. The CDU according to claim 10, wherein the legs are pivotally secured to said bottom of the container such that when said legs are in their first inoperative position said legs are contained underneath the CDU and when said legs are in their second operative position stabilizing said CDU, the distal end of each leg is positioned away from the container.

12. The CDU according to claim 11, further comprising a detent being provided on a leg such that when said legs are positioned in the second operative position stabilizing the container, the detent contacts a lower wall portion of the container to retain said legs in the second operative position stabilizing the container.

13. The CDU according to claim 12, wherein the bottom of the container is provided with a depression which receives said detent of said leg when said leg is in the first inoperative non-stabilizing position to prevent inadvertent movement of said legs from the first position to the second operative position.

14. The CDU according to claim 13, wherein the bottom of the container includes a base support member depending therefrom opposite the side where the legs are pivotally secured to the container bottom, said base support member assisting the legs in stabilizing the CDU when said legs are in the second operative position stabilizing the CDU.

15. The CDU according to claim 14, wherein a leg further includes a cutout adjacent its distal end such that when the legs are in the first non-stabilizing position, said leg abuts cooperatively against said base support member to allow said legs to fit completely underneath said CDU.

16. The CDU according to claim 10, further comprising:

the container having a side wall with a pair of generally parallel vertical slots provided therein; and each leg being pivotally attached to a pivot pin about their proximal ends which is slideably received within the vertical slots such that when said legs are in the first inoperative non-stabilizing position said legs are parallel and adjacent each other, and when the distal end of either leg is pulled out and radially away from the container, the other leg moves in a similar manner due to the interaction between the respective gear teeth of each leg and the pivot pins of each leg slides downwardly in their respective slots until the legs have rotated through a complete 90 degrees and the legs are in the second operative position stabilizing the CDU.

\* \* \* \* \*